United States Patent
Feng et al.

(10) Patent No.: US 10,082,491 B2
(45) Date of Patent: Sep. 25, 2018

(54) PEARL GRADING METHOD

(71) Applicants: ZHEJIANG UNIVERSITY OF SCIENCE AND TECHNOLOGY, Hangzhou (CN); ZHEJIANG RUANS PEARL LIMITED COMPANY, Shaoxing (CN)

(72) Inventors: Xi Feng, Hangzhou (CN); Yang Shi, Hangzhou (CN); Aihua Yu, Hangzhou (CN)

(73) Assignee: ZHEJIANG UNIVERSITY OF SCIENCE AND TECHNOLOGY, Hangzhou (CN)

( * ) Notice: Subject to any disclaimer, the term of this patent is extended or adjusted under 35 U.S.C. 154(b) by 0 days.

(21) Appl. No.: 15/529,492

(22) PCT Filed: Jul. 14, 2015

(86) PCT No.: PCT/CN2015/083938
§ 371 (c)(1),
(2) Date: May 24, 2017

(87) PCT Pub. No.: WO2016/183921
PCT Pub. Date: Nov. 24, 2016

(65) Prior Publication Data
US 2017/0261486 A1    Sep. 14, 2017

(30) Foreign Application Priority Data
May 21, 2015 (CN) .......................... 2015 1 0261943

(51) Int. Cl.
| | | |
|---|---|---|
| G06K 9/00 | (2006.01) | |
| G01N 33/38 | (2006.01) | |
| G06T 7/40 | (2017.01) | |
| G06K 9/46 | (2006.01) | |
| G01N 21/64 | (2006.01) | |
| G01N 21/89 | (2006.01) | |
| G01N 21/87 | (2006.01) | |

(52) U.S. Cl.
CPC ....... *G01N 33/381* (2013.01); *G01N 21/6456* (2013.01); *G01N 21/87* (2013.01); *G01N 21/8914* (2013.01); *G06K 9/469* (2013.01); *G06T 7/40* (2013.01)

(58) Field of Classification Search
CPC ........ G01N 21/57; G01N 21/25; G01N 21/87; G01N 21/6456; G01N 21/8914; G01N 33/381; G01J 3/51; A47G 1/06; A47G 1/0633; A47G 1/0638; G06K 9/469; G06T 7/40
See application file for complete search history.

(56) References Cited

U.S. PATENT DOCUMENTS

| | | | | |
|---|---|---|---|---|
| 6,020,954 A | * | 2/2000 | Aggarwal | G01N 21/87 356/30 |
| 9,222,893 B2 | * | 12/2015 | Hornabrook | G01N 21/87 |
| 9,903,852 B2 | * | 2/2018 | Nagai | G01N 33/381 |
| 2009/0038513 A1 | * | 2/2009 | Lin | C09C 1/0015 106/417 |
| 2012/0050526 A1 | * | 3/2012 | Nagai | G01N 21/55 348/125 |

FOREIGN PATENT DOCUMENTS

| | | |
|---|---|---|
| CN | 101007308 A | 8/2007 |
| CN | 102549411 A | 7/2012 |
| WO | WO2011058823 A1 | 5/2011 |

OTHER PUBLICATIONS

Tang, Yiping, et al. Pearl Online Detecting and Grading Device Based on Monocular Multi-view Machine Vision, Transactions of the Chinese Society for Agricultural Machinery, vol. 45, No. 1, Jan. 31, 2014, ISSN:1000-1298.

Tang, Yiping, et al. Evaluation of Pearl Quality Based on Monocular Multi-view Machine Vision, Transactions of the Chinese Society for Agricultural Machinery, vol. 45, No. 4, Apr. 30, 2014, ISSN:1000-1298.

Mamangkey, Noldy Gustaf F. "Assessing Pearl Quality Using Reflectance UV-Vis Spectroscopy: Does the Same Donor Produce Consistent Pearl Quality", Marine Drugs, vol. 8, Sep. 20, 2010, ISSN 1660-3397, pp. 2517-2525.

* cited by examiner

*Primary Examiner* — Ali Bayat
(74) *Attorney, Agent, or Firm* — Gokalp Bayramoglu

(57) ABSTRACT

A pearl grading method includes the following steps: (1) determining the color type of the pearl to be graded; (2) generating a simulated three-dimensional graph of the pearl to be graded; (3) calculating roundness, so as to obtain a roundness grade; (4) calculating the diameter of the simulated three-dimensional graph, so as to obtain a diameter grade; (5) drawing an illumination-wavelength reflection spectrum; (6) changing a detected part, and drawing an illumination-wavelength reflection spectrum again; (7) repeating the step (6) for at least two times; (8) performing weighted average to obtain a correction curve; and (9) comparing the correction curve with each glossiness grade spectrum baseline, so as to determine a glossiness grade according to the spectrum baseline with the highest coincidence degree. The method has the beneficial effects of low cost, high speed, good result consistency and high detection precision.

9 Claims, No Drawings

PEARL GRADING METHOD

CROSS REFERENCE TO RELATED APPLICATIONS

This application is the national phase entry of International Application No. PCT/CN2015/083938, filed on Jul. 14, 2015, which is based upon and claims priority to Chinese Patent Application No. 2015102619434 (CN), filed on May 21, 2015, the entire contents of which are incorporated herein by reference.

TECHNICAL FIELD

The present invention relates to the field of detection technology, specifically to a pearl grading method.

BACKGROUND

The parameters to determine the pearl grade are color, diameter, roundness, and glossiness. The color types of jewelry level pearl are mainly limited to few colors such as white, yellow, and so on. Currently, the determination of pearl grade needs highly specialized personnel with rich experience to sort by hand (It is necessary to select different tools according to color, diameter, roundness, and glossiness to determine the grade of each parameter. The diameter of the jewelry level pearl should be more than 9 mm. The pearl where a brightness difference of both sides of the pearl is visible to naked eyes does not belong to the jewelry level, etc.). If the grade is determined by carefully comparing the pearl to be graded with the standard pearl sample, too much time and labor will be consumed, and the efficiency is extremely low. Further, a suit of the standard pearl sample is expensive. Also, parameters such as the glossiness and so on of the standard pearl sample will degrade over time. Thus, after a certain period, the standard pearl sample needs to be re-purchased. The ordinary pearl culturing enterprise cannot afford. Moreover, the accuracy and consistency of hand sorting cannot be ensured.

SUMMARY OF THE INVENTION

The object of the present invention is to provide a pearl grading method aimed for the deficiency of the prior art.

A pearl grading method includes the steps as follows. (1) The color type of the pearl to be graded is determined via image identification technology. (2) A simulated three-dimensional graph of the pearl to be graded is generated via image identification technology. (3) The roundness of the simulated three-dimensional graph is calculated. The roundness grade of the pearl to be graded is obtained according to the threshold range of the corresponding roundness grade in which the roundness grade of the simulated three-dimensional graph falls. (4) The diameter of the simulated three-dimensional graph is calculated. The diameter grade of the pearl to be graded is obtained according to the threshold range of the corresponding diameter grade in which the diameter grade of the simulated three-dimensional graph falls. (5) An illumination-wavelength reflection spectrum of a detected part of the pearl to be graded is drawn. (6) The pearl to be graded is driven to rotate to change the detected part. An illumination-wavelength reflection spectrum of the detected part of the pearl to be graded is drawn again. (7) The step (6) is repeated at least twice. (8) A weighted average of the previous reflection spectrums of the pearl to be graded is calculated to obtain a correction curve. (9) The correction curve is compared with each glossiness grade spectrum baseline of the corresponding color type, the diameter grade, and the roundness grade, so as to determine a glossiness grade of the pearl to be graded according to the glossiness grade which corresponds to the spectrum baseline with the highest coincidence degree, so that the comprehensive grade can be determined.

Furthermore, in the step (1), the color type is determined via image acquisition data of at least three directions of the pearl to be graded. The step (1) further includes a pre-sorting step (1-0): when the difference value between the image acquisition data in two arbitrary directions is larger than a permissible threshold, the pearl to be graded is deemed as a non-jewelry level product which should be eliminated.

Furthermore, in the step (3), when the difference value between the calculated roundness grade and a boundary value of the threshold range of corresponding roundness grade is smaller than a certain value, the step of re-checking the roundness grade (3-1) is initiated. The roundness grade of the pearl to be graded is re-calculated. The roundness grade of the pearl to be graded is re-determined. Furthermore, the certain value is $\frac{1}{10}$ of the threshold range of roundness grade.

Furthermore, in the step (4), the diameter of the pearl to be graded is obtained. by calculating a weighted average of diameter sizes of simulating three-dimensional graphs in at least three directions. When the difference value between the calculated diameter and a boundary value of the threshold range of the corresponding diameter grade is smaller than a certain value, the step of re-checking diameter grade (4-1) is initiated. At least one direction which is different the previously three directions is selected to re-capture the diameter of the pearl to be graded. The weighted average of the re-captured diameter and the diameters obtained from the three previously directions is calculated to re-determine the diameter grade of the pearl to be graded.

Furthermore, the certain value is $\frac{1}{10}$ of the threshold range of diameter grade.

Furthermore, in the step (9), the correction curve is fitted with each glossiness grade spectrum baseline of corresponding color type, the diameter grade, and the roundness grade Iva linear regression technology. The point which has the largest wavelength difference value between the correction curve and the spectrum baseline with the highest coincidence degree is selected. When the difference value is larger than a certain value, the step of re-checking the glossiness grade (9-1) is initiated. The pearl is driven to rotate. At least three new detected parts that are different from the previously detected parts are selected to draw the illumination-wavelength reflection spectrum of the new detected parts of the pearl to be graded. The weighted average of the previous reflection spectrums of the pearl to be graded is calculated to obtain the second correction curve. The second correction curve is compared with corresponding glossiness grade spectrum baseline to re-determine the glossiness grade.

Furthermore, the curtain value of the wavelength difference value is $\frac{1}{100}$ of maximum limit value and minimum limit value of the wavelength curve.

Furthermore, the method further includes a step of database establishment (0-1). The color classification, roundness grade determination, diameter grade determination, and glossiness grade determination are conducted on the standard pearl sample is conducted by image identification and spectral analysis technologies.

The beneficial effects of the method are as follows. Image identification and spectral analysis technologies are used to automatically grade the pearl to be graded. The method has a low cost, a high speed, a good result consistency, and a high detection precision.

DETAILED DESCRIPTION OF THE INVENTION

Hereinafter, the present invention is further described in detail with reference to embodiments.

The pearl grading method of the present invention includes the steps as follows. (1) The color type of the pearl to be graded is determined via image identification technology. (2) A simulated three-dimensional graph of the pearl to be graded is generated via image identification technology, (3) The roundness of the simulated three-dimensional graph is calculated. The roundness grade of the pearl to be graded is obtained according to the threshold range of the corresponding roundness grade in which the roundness grade of the simulated three-dimensional graph falls. (4) The diameter of the simulated three-dimensional graph is calculated. The diameter grade of the pearl to be graded is obtained according to the threshold range of the corresponding diameter grade in which the diameter grade of the simulated three-dimensional graph falls. (5) An illumination-wavelength reflection spectrum of a detected part of the pearl to be graded is drawn. (6) The pearl to be graded is driven to rotate to change the detected part. An illumination-wavelength reflection spectrum of the detected part of the pearl to be graded is drawn again. (7) The step (6) is repeated at least twice. (8) A weighted average of the previous reflection spectrums of the pearl to be graded is calculated to obtain a correction curve. (9) The correction curve is compared with each glossiness grade spectrum baseline of the corresponding color type, the diameter grade, and the roundness grade, so as to determine a glossiness grade of the pearl to be graded according to the glossiness grade which corresponds to the spectrum baseline with the highest coincidence degree, so that the comprehensive grade can be determined. Since the image identification and spectral analysis technologies are mature and are widely used in various manufacture and processing industry, though these technologies are not applied in the pearl grading field currently, the basic principle remains the same, so the specific details are not included here.

In the step (1), the color type is determined via image acquisition data of at least three directions of the pearl to be graded. The step (1) further includes a pre-sorting step (1-0): when the difference value between the image acquisition data in two arbitrary directions is larger than a permissible threshold, the pearl to be graded is deemed as a non-jewelry level product which should be eliminated.

In the step (3), when the difference value between the calculated roundness grade and a boundary value of the threshold range of corresponding roundness grade is smaller than a certain value, the step of re-checking the roundness grade (3-1) is initiated. The roundness grade of the pearl to be graded is re-calculated. The roundness grade of the pearl to be graded is re-determined. In the embodiment, the certain value is $1/10$ of the threshold range of roundness grade. The value also can be adjusted based on the natural environmental conditions and precision requirements.

In the step (4), the diameter of the pearl to be graded is obtained by calculating a weighted average of diameter sizes of simulating three-dimensional graphs in at least three directions. When the difference value between the calculated diameter and a boundary value of the threshold range of the corresponding diameter grade is smaller than a certain value, the step of re-checking diameter grade (4-1) is initiated. At least one direction which is different the previously three directions is selected to re-capture the diameter of the pearl to be graded. The weighted average of the re-captured diameter and the diameters obtained from the three previously directions is calculated to re-determine the diameter grade of the pearl to be graded. In the embodiment, the certain value is $1/10$ of the threshold range of diameter grade. The value also can be adjusted based on the natural environmental conditions and precision requirements.

In the step (9), the correction curve is fitted with each glossiness grade spectrum baseline of corresponding color type, the diameter grade, and the roundness grade via linear regression technology. The point which has the largest wavelength difference value between the correction curve and the spectrum baseline with the highest coincidence degree is selected. When the difference value is larger than a certain value, the step of re-checking the glossiness grade (9-1) is initiated. The pearl is driven to rotate. At least three new detected parts that are different from the previously detected parts are selected to draw the illumination-wavelength reflection spectrum of the new detected parts of the pearl to be graded. The weighted average of the previous reflection spectrums of the pearl to be graded is calculated to obtain the second correction curve. The second correction curve is compared with corresponding glossiness grade spectrum baseline to re-determine the glossiness grade. In order to improve the detection accuracy, the curtain value of the wavelength difference value is $1/100$ of the maximum limit value and the minimum limit value of the wavelength curve.

Before grading, the method further includes a step of database establishment (0-1). The color classification, roundness grade determination, diameter grade determination, and glossiness grade determination are conducted on the standard pearl sample is conducted by image identification and spectral analysis technologies.

Although the present invention is shown and described with reference to the preferred embodiment, the ordinary skilled person in the art should understand that the present invention is not limited to the description of the embodiment. Various changes of formation and detail can be made within the scope of the claims.

What is claimed is:

1. A pearl grading method, comprising the following steps:
   (1) determining a color type of a pearl to be graded via image identification technology;
   (2) generating a simulated three-dimensional graph of the pearl to be graded via the image identification technology;
   (3) calculating a roundness of the simulated three-dimensional graph; obtaining a roundness grade of the pearl to be graded according to a threshold range of corresponding roundness grade in which the roundness of the simulated three-dimensional graph falls;
   (4) calculating a diameter of the simulated three-dimensional graph; obtaining a diameter grade of the pearl to be graded according to a threshold range of corresponding diameter grade in which the diameter of the simulated three-dimensional graph falls;
   (5) drawing an illumination-wavelength reflection spectrum of a detected part of the pearl to be graded;
   (6) driving the pearl to be graded to rotate to change the detected part; drawing an illumination-wavelength reflection spectrum of the detected part of the pearl to be graded again;

(7) repeating the step (6) at least twice;

(8) calculating a weighted average of previous reflection spectrums of the pearl to be graded to obtain a correction curve; and (9) comparing the correction curve with each glossiness grade spectrum baseline of the corresponding color type, the diameter grade, and the roundness grade, so as to determine a glossiness grade of the pearl to be graded according to a glossiness grade which corresponds to the spectrum baseline with the highest coincidence degree, so that a comprehensive grade is determined.

2. The pearl grading method of claim 1, wherein the step (1) further comprises, determining the color type via image acquisition data of at least three directions of the pearl to be graded; and a pre-sorting step (1-0): when a difference value between image acquisition data in two arbitrary directions is larger than a permissible threshold, deeming the pearl to be graded as a non-jewelry level product to be eliminated.

3. The pearl grading method of claim 1, wherein in the step (3), when a difference value between the calculated roundness and a boundary value of the threshold range of the corresponding roundness grade is smaller than a certain value, initiating a step of re-checking the roundness grade (3-1), and the step (3) further includes:

re-calculating the roundness of the pearl to be graded; and re-determining the roundness grade of the pearl to be graded.

4. The pearl grading method of claim 3, wherein the certain value is $1/10$ of the threshold range of the roundness grade.

5. The pearl grading method of claim 1, wherein the step (4) further comprises, obtaining the diameter of the pearl to be graded by calculating a weighted average of diameter sizes of the simulated three-dimensional graphs in at least three directions;

when a difference value between the calculated diameter and a boundary value of the threshold range of the corresponding diameter grade is smaller than a certain value, initiating a step of re-Checking diameter grade (4-1), which includes:

selecting at least one direction which is different from three previous directions to re-capture a diameter of the pearl to be graded; and calculating a weighted average of the re-captured diameter and diameters obtained from the three previous directions to re-determine the diameter grade of the pearl to be graded.

6. The pearl grading method of claim 5, wherein the certain value is $1/10$ of the threshold range of the diameter grade.

7. The pearl grading method of claim 1, wherein the step (9) further comprises, fitting the correction curve with each glossiness grade spectrum baseline of the corresponding color type, the diameter grade, and the roundness grade via linear regression technology;

selecting a point which has the largest wavelength difference value between the correction curve and the spectrum baseline with the highest coincidence degree;

when the difference value is larger than a certain value, initiating a step of re-checking the glossiness grade (9-1), which includes:

driving the pearl to be graded to rotate;

selecting at least three new detected parts that are different from previously detected pails to draw an illumination-wavelength reflection spectrum of the new detected parts of the pearl to be graded;

calculating a weighted average of the previous reflection spectrums of the pearl to be graded to obtain a second correction curve; and comparing the second correction curve with the corresponding glossiness grade spectrum baseline to re-determine the glossiness grade.

8. The pearl grading method of claim 7, wherein the certain value of the wavelength difference value is $1/100$ of a maximum limit value and a minimum limit value of the wavelength curve.

9. The pearl grading method of claim 1, wherein the pearl grading method further comprises a step of database establishment (0-1): conducting color classification, roundness grade determination, diameter grade determination, and glossiness grade determination on the standard pearl sample via image identification technology and spectral analysis technology.

* * * * *